US006110102A

United States Patent [19]

[11] Patent Number: 6,110,102

[45] Date of Patent: Aug. 29, 2000

Harrison

[54] VISION OF LOVE

[76] Inventor: Michael A. Harrison, 5221 Sawyer Dr., Cameron, N.C. 28326

[21] Appl. No.: 09/314,932

[22] Filed: May 20, 1999

[51] Int. Cl.[7] .................................. A61F 5/00; A61H 1/00

[52] U.S. Cl. .................................................. 600/38; 601/46

[58] Field of Search .................................. 600/38, 39, 41; 601/46

[56] References Cited

U.S. PATENT DOCUMENTS 3,626,931 12/1971 Bysakh .
3,669,100 6/1972 Csanad .
5,176,130 1/1993 Kim .......................................... 128/36
5,519,593 5/1996 Hasness .
5,725,473 3/1998 Taylor .

OTHER PUBLICATIONS printed from Adam and Eve Online Catalog, Glow–In–The––Dark Slim Line, p. 1, Oct. 17, 1997.

*Primary Examiner*—Eric F. Winakur
*Assistant Examiner*—Catherine McPherson
*Attorney, Agent, or Firm*—Patent & Trademark Services; Joseph H. McGlynn

[57] ABSTRACT

A marital aid containing an elongated shaft which is transparent, and which has a vibrating motor which vibrates the shaft and an internal source of illumination which shines through the transparent shaft.

2 Claims, 1 Drawing Sheet

VISION OF LOVE

BACKGROUND OF THE INVENTION

This invention relates, in general, to vibrators, and, in particular, to a vibrator which has internal illumination.

DESCRIPTION OF THE PRIOR ART

In the prior art various types of vibrators have been proposed. For example, U.S. Pat. No. 3,626,931 to Bysakh discloses a vibrator device comprising an outwardly tapering sleeve and an extension for vibrating the female erotic parts.

U.S. Pat. No. 3,669,100 to Csanad discloses a electrically operated vibrator for treating female disorders in female animals having means for gradually releasing medications such as hormone gels and antibiotics.

U.S. Pat. No. 5,519,593 to Hasness discloses a combination lightwand and holster device in which a cone shaped diffuser element expands to form a holster when not in use.

U.S. Pat. No. 5,725,473 to Taylor discloses a sexual aid including a housing mounted on detachable legs and a vibrating motor.

SUMMARY OF THE INVENTION

The present invention is directed to a marital aid containing an elongated shaft which is transparent, and which has a vibrating motor which vibrates the shaft and an internal source of illumination which shines through the transparent shaft.

It is an object of the present invention to provide a new and improved marital aid which is transparent and has internal illumination.

It is an object of the present invention to provide a new and improved marital aid which has a vibrating motor.

It is an object of the present invention to provide a new and improved marital aid which has a shaft which is vibrated by a motor.

These and other objects and advantages of the present invention will be fully apparent from the following description, when taken in connection with the annexed drawings.

DESCRIPTION OF THE PREFERRED EMBODIMENT

Figure 1:
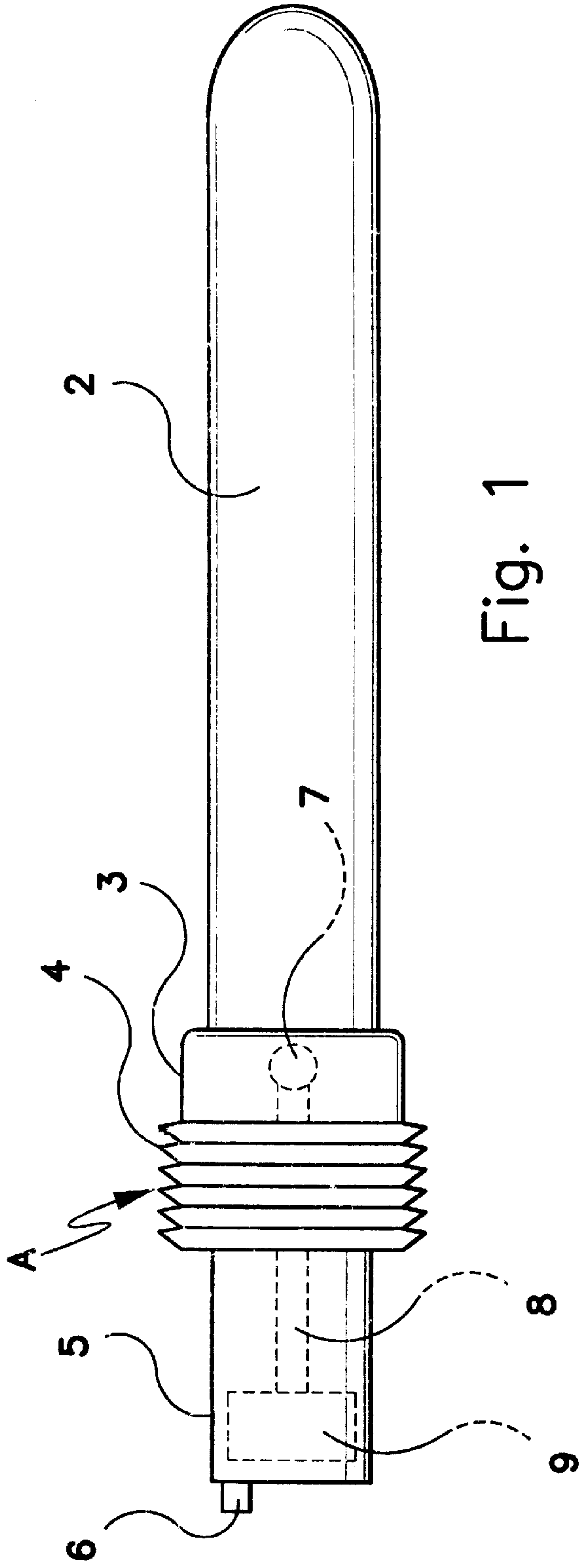
FIG. 1 is side view of the present invention.

Referring now to the drawings in greater detail, FIG. 1 shows the illuminated vibrator of the present invention. The vibrator has an elongated shaft 2 which is made from a transparent material such as plastic. Below the shaft 2 is a housing 3 which may also be made from transparent material or it can be made from opaque material. Secured to the housing 3 is a rotatable ring 4 which can be rotated in the direction of the arrow A in FIG. 1 to turn on or off the vibrating motor 9 which is mounted in the handle 5 of the device.

Figure 2:
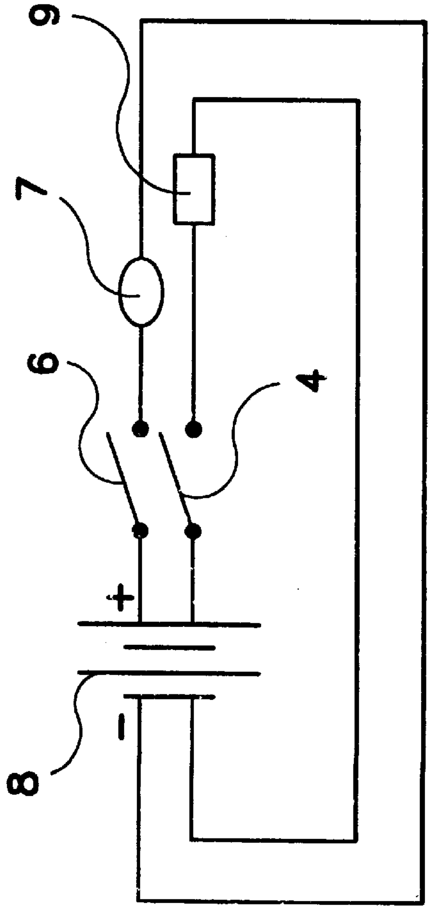
FIG. 2 is a schematic view of the electrical circuitry used with the present invention.

The housing 3 has a bulb 7 electrically and mechanically mounted therein by any conventional means such as a light bulb socket. The bulb is electrically connected to a switch 6 mounted in the handle 5 and the switch is in turn electrically connected to a battery 8, as shown in FIG. 2. When the switch 6 is turned on the bulb will be lit by the battery and since the shaft 2 is transparent, the light from the bulb will shine through the shaft 2.

The handle 5 also has a vibrating motor 9 mounted therein, again by any conventional mounting means. The vibrating motor 9 is electrically connected to the battery 8 via a rotating switch 4 which is also the rotating ring shown in FIG. 1. When the ring 4 is turned ¼ turn in the direction of the arrow A, the motor 9 is turned on and the shaft 2 will vibrate. When the ring 4 is turned ¼ turn in the opposite direction of the arrow A, the motor 9 is turned off and the shaft 2 will stop vibrating.

The handle 5 and the ring 4 can be detachably secured together by any conventional means, such as complimentary screw threads (not shown) which will allow the handle 5 and the ring 4 to be separated so the battery can be replaced if and when necessary.

In use a person could turn on the bulb 7 by means of the switch 6 which will allow the light from bulb 7 shine through the transparent shaft 2. Since the bulb 7 and the motor 9 are connected to the battery 8 by parallel circuits, the bulb and the motor can be operated separately.

If desired the user could also turn on the motor 9 by rotating the ring 4 and the motor would cause the shaft 2 to vibrate. Therefore, the bulb or the motor could be operated separately or together depending on whether the switches 6, 4 are turned on or off.

For illustration purposes only, the length of the shaft is 8 inches and the diameter of the shaft is 1½ to 2 inches, although other dimensions could be used without departing from the scope of the invention.

Although the Vision of Love and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A marital aid apparatus comprising:

a shaft made entirely from transparent material, a housing attached to said shaft, a light bulb mounted within said housing, a ring rotatably attached to said housing, said ring having a handle detachably secured thereto, a source of electrical power mounted within said handle, means for vibrating said shaft mounted within said handle, first switch means on said handle for turning said bulb on and off, second switch means for turning said means for vibrating on and off.

2. The marital aid apparatus as claimed in claim 1, and wherein said ring is rotated in one direction to turn said means for vibrating on, and is rotated in another direction to turn said means for vibrating off.

* * * * *